(12) United States Patent
Marchese et al.

(10) Patent No.: US 11,478,657 B1
(45) Date of Patent: *Oct. 25, 2022

(54) LED THERAPY BED

(71) Applicants: Steve Marchese, Irvine, CA (US);
Chase Marchese, Irvine, CA (US)

(72) Inventors: Steve Marchese, Irvine, CA (US);
Chase Marchese, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/378,697

(22) Filed: Jul. 17, 2021

(51) Int. Cl.
*A61N 5/06* (2006.01)
*A61N 5/00* (2006.01)

(52) U.S. Cl.
CPC ......... *A61N 5/0616* (2013.01); *A61N 5/0625* (2013.01); *A61N 2005/005* (2013.01); *A61N 2005/0627* (2013.01); *A61N 2005/0629* (2013.01); *A61N 2005/0638* (2013.01); *A61N 2005/0652* (2013.01); *A61N 2005/0659* (2013.01); *A61N 2005/0663* (2013.01)

(58) Field of Classification Search
CPC ....... A61N 5/0613–2005/0642; A61N 5/0616; A61N 5/0625; A61N 2005/005; A61N 2005/0627; A61N 2005/0629; A61N 2005/0638; A61N 2005/0652; A61N 2005/0659; A61N 2005/0663
See application file for complete search history.

(56) References Cited

U.S. PATENT DOCUMENTS

| | | | |
|---|---|---|---|
| 9,913,994 B2 | 3/2018 | Marchese et al. | |
| 10,363,434 B2 | 7/2019 | Marchese et al. | |
| 11,090,248 B2 * | 8/2021 | Finnen | A61K 8/46 |
| 2019/0183770 A1 * | 6/2019 | Finnen | A61K 8/36 |

OTHER PUBLICATIONS

Walle, 5 Ways Nitric Oxide Supplements Boost Your Health and Performance, Mar. 25, 2018; https://www.healthline.com/nutrition/nitric-oxide-supplements (Year: 2018).*

* cited by examiner

*Primary Examiner* — Jonathan T Kuo

(57) ABSTRACT

A light therapy bed including multiple LEDs positioned in individually controllable modules is disclosed. The modules of LEDs are configured to have direct contact or in close proximity to the skin or tissue of the user, through an acrylic or similar cover. The LEDs light the surface and underlying layers of tissue for photodynamic stimulation of the cells. Iterations of the device utilize light known to have a bactericidal effect in the case of acne, MRSA, etc. The bed is fabricated and formed in a curved configuration to optimize contact between the LEDs and the skin of a user. Each of the LED modules may be mounted with a PCB in an arrangement to provide even lighting and temperature upon the skin or tissue surface of a user. Each module also has one or more thermal sensors that evenly and quickly heat all of the areas of a user's body.

2 Claims, 10 Drawing Sheets

LED THERAPY BED

CROSS-REFERENCE TO RELATED APPLICATIONS

None

FEDERALLY SPONSORED RESEARCH

None

BACKGROUND

Field of the Invention

The invention relates to a Light Emitting Diode (LED) Light Therapy Bed. Specifically, the invention relates to a Light Therapy Bed which treats, among numerous other medical conditions, high blood pressure. Exemplary embodiments of the invention relate to improvements in a light emitting diode (LED) therapy bed. More particularly, the LED therapy bed provides a dermal therapy bed that can provide health benefits to a person by elevating and maintaining the therapy temperature of a person on the beds a source of bio-stimulative, non-coherent, non-monochromatic light.

Exemplary embodiments of this invention relate to improvements in medical devices For topical photodynamic therapy (POT) treatment of patients. Specifically, exemplary embodiments relate to a rigid surface (circuit board) containing LEDs as a source of bio-stimulative, non-coherent, non-monochromatic light, which are placed in contact or in close proximity with the patient's skin or tissue, and a method for making that apparatus.

Description of the Related Art

Nonmonochromatic light as defined wavelengths has produced beneficial bio-stimulative effects and has been known to trigger specific biological functions, such as increased rate of metabolism, photo-repair and cell division. Stimulation has occurred, however, with light emitted in specific wavelengths.

While the exact mechanism by which the beneficial bio-stimulative effects have been achieved is not precisely known, several theories have been put forth. It has been suggested that non-monochromatic light emitted in the range of about 415 nm to about 940 nm penetrates body tissue and is absorbed, reflected and scattered to excite molecules within cells and tissue to thereby accelerate repair and regeneration. It is known, however, that light in the range of about 415 nm to about 465 nm has a bactericidal effect, thereby relieving the appearance of bacteria induced acne.

A further theory suggests that different cells have different photoreceptors, which respond to only particular wavelengths of light. This theory supports the phenomenon that the application of only certain wavelengths of light result in bio-stimulative effects and the resulting stimulation of the dermis and an increase of collagen and elastin production With respect to similar but non-LED technology, light therapy has utilized lasers with relatively low power and bio-stimulative treatment utilizing lasers has been referred to as "soft" laser therapy. In such applications, low level laser energy radiation has been successfully employed to stimulate wound healing and treatment of musculoskeletal disorders and skin ulcers.

It has been previously theorized that the properties of laser radiation, which resulted in the beneficial bio-stimulative effects of soft laser therapy, were the monochromaticity and coherence of laser radiation.

In a prior invention, Applicant noted that if bio-stimulative light effects were compounded by combining into one device four different wavelengths of light, each with known benefits, that the effects could be greater than if each wavelength was applied separately, and that close proximity of the LEDs to the user promoted uniform coverage of the target area, in order to receive all wavelengths simultaneously, and more effective penetration of light.

Therapy beds have taken a variety of shapes acid functions over the years. Some early therapy beds claimed to provide the health benefits of the sun, while later versions provided mostly tanning effects to the skin of the user.

A number of patents and/or publications relate to these issues. Exemplary examples of patents and/or publications that try to address this/these issue(s) are identified and discussed below.

U.S. Pat. No. 10,363,434 discloses a Light Therapy Bed which has similar claims and invention to U.S. Pat. No. 9,913,994.

U.S. Pat. No. 9,913,994 discloses a Light Therapy Bed.

U.S. Pat. No. 6,896,693 discloses a "Photo-Therapy Device." The photo-therapy device of the patent operates up to several feet from the user.

U.S. Pat. No. 8.425,577 discloses a "LED Photherapy Apparatus." This patent uses red and near infra-red light to provide phototherapy. This patent uses an acrylic support that spaces the LEDs from the user and further distances the LEDs from the user with a top cover that is distanced from the user.

U.S. Publication No. 2009/0222070 discloses a "Capsule with Whole Body LED Photo-therapy System."

Known LED beds appear to be based on retrofitted tanning beds. This design raises several issues which include:

1). Tanning beds having a clamshell design and a top portion which may sit too far away from the body for LEDs to effectively penetrate the body of a user and deliver therapeutic energy. The bottom portion of a retrofitted tanning bed may have the same problem with proximity because the LEDs may sit too far away from the body for optimal efficacy.

2). An acrylic cover of a tanning bed may distort the preset angle being emitted by the LEDs and may also reduce power output.

3). With a LED bed that is retrofitted from a tanning bed, it may be impracticable or impossible to simultaneously raise the temperature of all parts of the human body because the torso would heat up and get hotter than the legs or the arms, and in some instances even the legs would heat up faster and get hotter than the arms. This drawback may negatively affect the ability to obtain FDA clearance for a retrofitted tanning bed type LED bed.

At a distance of several inches between the LEDs and the user, the temperature needed to elevate the skin to obtain skin dilation and further provide the best penetration of phototherapy may be difficult, impractical or even impossible to obtain. In such an application, to benefits provided by the LEDs may be reduced by the support and the distance between the user and the LEDs. What is needed is a phototherapy device that provides regulated skin temperature so that all areas of the body can be brought up to a therapeutic temperature level simultaneously and held at that temperature, and which can do so regardless of non-optimum environmental conditions like ambient temperature; and further provides very close dermal phototherapy to the light sources. It is believed in the related art that releasing nitric oxide stored in the body could provide lowering of blood pressure in a patient.

SUMMARY OF THE CLAIMED INVENTION

An aspect of exemplary embodiments of the present invention is to provide a light therapy system of the general character described which improves upon the above-described limitations and drawbacks of the above-described prior art.

To solve the problem of LEDs being spaced too far from the patient, exemplary embodiments of the invention provide a custom designed bottom portion that has the LEDs virtually right up against an acrylic or other material cover, such that the LEDs are only about ¼-½ inch from the user's body, where a user would treat one side of their body and then flip over and treat the other side of their body. Alternatively, both sides of a user's body can be treated at the same time by having another bed positioned above the user that can be lowered into contact or near contact with the user.

To solve the problem of distortion of the angle of LED energy being emitted, Applicant provides an acrylic which does not distort or minimizes distortion of the angle of the LED energy being emitted, and which lets almost all of the energy pass through to the user for therapeutic effect. Examples of known acrylic are a transparent or ultra-transparent acrylic.

To solve the problem of having a different temperature of different parts of a user's body, where, for example, a user's arms or legs may be at a different temperature than the user's torso, and the problem of different environmental or other conditions causing different body temperatures, Applicant has provided modules of LEDs which may be controlled individually or in groups, so that one part of the user will not be at too high or too low a temperature, compared to other parts of the user's body. In order to gain FDA clearance, it is necessary to simultaneously raise the temperature of all parts of the human body, e.g., the torso, the legs, the arms, neck, etc. Additionally, these modules are able to maintain the temperature regardless of normal variations in environmental or other conditions, like ambient temperature.

According to an exemplary embodiment, a LED therapy bed includes a support frame having a plurality of rails. The plurality of rails form a curved support. The rails support a plurality of separately controlled LED modules, where each module has a plurality of LEDs regulated by a current limiting circuit. Said plurality of LEDs being overdriven to increase light output beyond normal operating intensity and to further produce thermal heat from said plurality of LEDs in order to produce a skin temperate of a user of between 97 and 108 degrees Fahrenheit from direct thermal conduction. Each module further including at least one thermal sensor that locally senses a temperature of said module; and each module further including at least one fan wherein said fan speed is regulated directly or indirectly by said at least one temperature sensor. A master controller that controls each said module LEDs, the thermal sensor and the at least one fan; wherein the temperature of each module can be separately controlled.

According to another exemplary embodiment, a LED therapy bed includes a support frame having a plurality of rails forming a curved support. The rails support a plurality of separately controlled LED modules.

Each module has a plurality of LEDs regulated by a current limiting circuit. The plurality of LEDs being overdriven to increase light output beyond normal operating intensity and to further produce thermal heat from said plurality of LEDs in order to produce a skin temperate of between 97 and 108 degrees Fahrenheit from direct thermal conduction. Each LED module further including at least one thermal sensor that locally senses a temperature of said module.

Each module further including at least one fan wherein said fan speed is regulated directly or indirectly by said at least one temperature sensor, and a master controller that controls the LEDs, the at least one fan and the at least one temperature sensor in each said module, wherein the temperature and illumination of each module can be separately controlled.

According to another exemplary embodiment, a LED therapy bed includes a support frame having a plurality of rails forming a curved support. The rails support a plurality of LED modules. Each module having a plurality of LEDs regulated by one or more current limiting circuits. The plurality of different colored LEDs being overdriven to increase light output beyond normal operating intensity and to further produce thermal heat from said plurality of LEDs in order to produce a skin temperate of a user of between 97 and 108 degrees Fahrenheit from direct thermal conduction.

Each LED module further including at least one thermal sensor that locally senses a temperature of said module. Examples of known acrylic are transparent or ultra-transparent acrylic. However, other acrylics may be used as well. The cover is located over the top of the LEDs and space the LEDs from the user. Each module further including at least one fan wherein said fan speed is regulated directly or indirectly by said at least one temperature sensor. A master controller controls the LEDs, the at least one fan and the at least one thermal sensor in each module; wherein the temperature of each module can be separately controlled.

It is an object of the LED therapy bed to comprise a system for light therapy which utilizes non-coherent light generated by an array of LEDs which are confined within a bandwidth of about 415 nm to about 940 nm. The diode array is configured in a matrix to direct the light onto a diffused area of the user without utilizing an optical system or any intermediary material other than the acrylic layer. The LEDs rest directly on, or in close proximity to, the user through the use of the acrylic or similar layer. The LED therapy bed also lowers blood pressure It is an object of the LED therapy bed to overdrive the LEDs to create heat that is conducted to the skin of the user to provide heat in addition to the light therapy. In some exemplary embodiments, a single current regulating, limiting device or a single resistor may be used to consistently limit the current to all of the LEDs and provide both even illumination and heat.

It is another object of the LED therapy bed to provide a light therapy system of the general character described, which produces beneficial bio-stimulative effects.

It is another object of the LED therapy bed to provide a light therapy method of the general character described whereby non-coherent and non-monochromatic light within a wavelength range of about 415 nm to about 940 nm is employed for photo-bio-stimulation.

It is another object of the LED therapy bed to provide a light therapy method of the general character described which utilizes non-coherent and non-monochromatic light emanating from the LEDs.

It is another object of the LED therapy bed to include multiple modules of LED banks where each bank includes an individual thermal control of the module to maintain optimal skin dilation temperature. In one exemplary embodiment, each module includes 608 LEDs arranged in 19 rows by 32 columns. However, the exemplary embodiments are not limited to this particular exemplary embodiment and a thermal control may control more than one module, as would be understood by one of ordinary skill in the art.

It is still another object of the exemplary embodiments that the LED therapy bed may have an open top surface that does not cover over a person. Such an exemplary embodiment includes LEDs under the user where the small distance between the LEDs and the user can be maintained. Each bed has banks of modules are arranged in five rows by six columns. However, the invention is not limited to this structure and more or less columns and/or rows may be provided, including patterns other than columns and/or rows, such as circular shape, chevron shape, diagonal shape, etc.

It is a further object of the exemplary embodiments to have one or more fans for cooling individual modules in order to regulate the temperature transmitted to the acrylic cover 49. The benefits of the LEDs are logarithmically proportional to the distance between the LED and the user. In addition, the instant invention provides that by using four different wavelengths all together, at exactly the same time, a highly statistically significant reduction in both systolic and diastolic reduction in blood pressure is achieved.

Various objects, features, aspects and advantages of the present invention will become more apparent from the following detailed description of exemplary embodiments of the invention, along with the accompanying drawings in which like numerals represent like components.

DETAILED DESCRIPTION OF THE EXEMPLARY EMBODIMENTS

Figure 1:
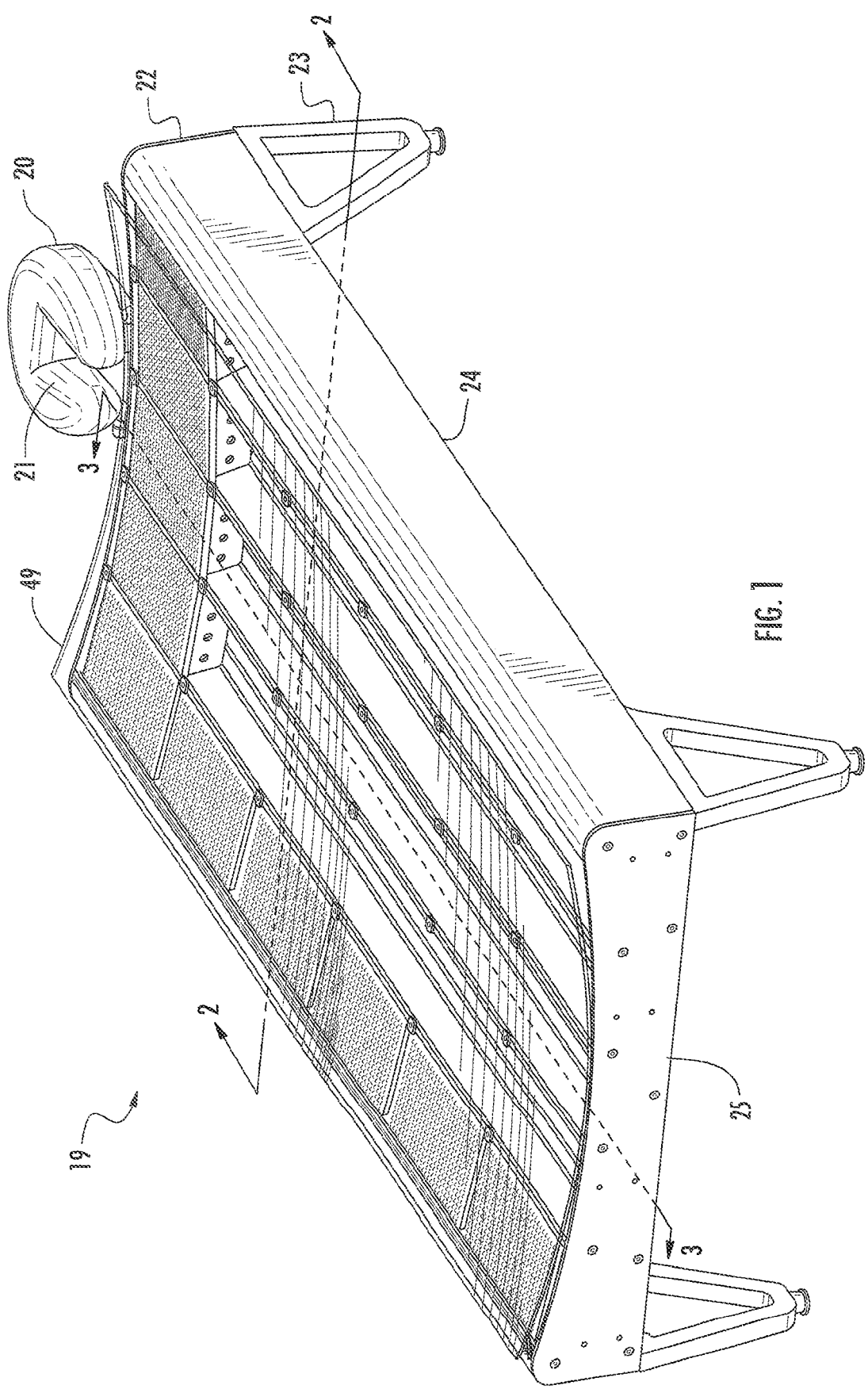
FIG. 1 illustrates a perspective view of a LED therapy bed.

For the purposes of promoting an understanding of the principles of the invention, reference will now be made to exemplary embodiments illustrated in the drawings and specific language will be used to describe the same. It will nevertheless be understood that no limitation of the scope of the invention is hereby intended. Any alterations and further modifications of the principles of the invention as described herein are contemplated and would normally occur to one of ordinary skill in the art to which the invention relates.

Turning to FIG. 1, this figure shows a perspective view of an LED therapy bed 19, according, to an exemplary embodiment. The LED therapy bed 19 is configured as having an open top structure. A plurality of legs 23 suspends a frame structure above the ground. The frame structure has front and rear frame members 22 and 25 with elongated side members 24 there between. As shown in FIG. 1, the bed has a plurality of modules 40, as discussed below in further detail. At one or both ends of the therapy bed 19 is a head rest/face rest 20 which has inner side supports 21. Element 20 serves as a headrest when a user is laying on their back on the LED therapy bed and serves as a face rest when a user is laying face down on the LED therapy bed 19. A space between the inner side supports 21 serves to receive the face of a user who is laying face down on the LED therapy bed 19. As additionally shown in FIG. 1, an acrylic cover 49 rests on the LED therapy bed 19 and is between the user and the LED modules 40.

The acrylic cover or layer 49 is designed to lower the temperature between the bottom of the cover, which rests on the LEDs and the frame of the modules and the temperature of the top of the cover, which receives the body of the user. The temperature of the top of the acrylic cover 49 which receives the body of the user is at a temperature of between 97-108° F., depending on the therapy to be provided. Although an acrylic cover is disclosed, other suitable materials may be used for a transparent or nearly transparent acrylic cover that rests on the LEDs in the LED modules. In the exemplary embodiment illustrated, the weight of the user presses down on the acrylic layer 49 such that the LEDs are in contact with the body through the acrylic layer.

Figure 2:
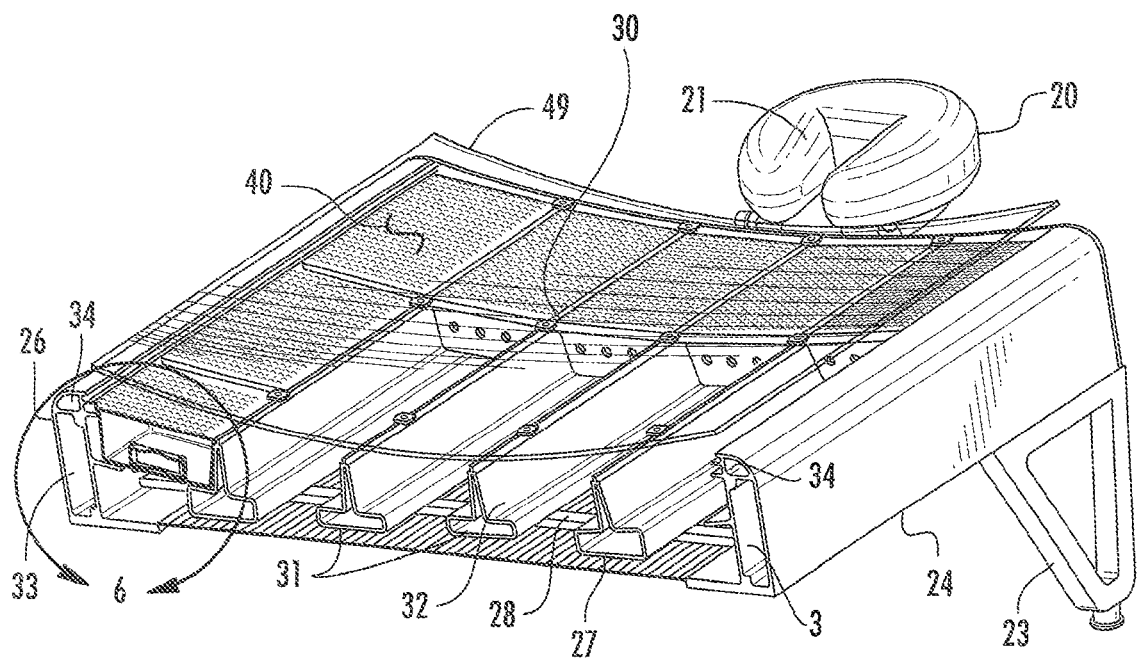
FIG. 2 illustrates a perspective cross-sectional view of the LED therapy bed, taken along lines 2-2 of FIG. 1.

Turning to FIG. 2, this figure is a perspective view taken along lines 2-2 in FIG. 1. In this figure, lengthwise extending frame members extend from one end of the therapy bed 19 to an opposite end. The frame members have an upper portion which is in an inverted "V" shape. Connected to the bottom of each inverted frame member is a horizontally extending member 31.

Two horizontally extending members in the center portion are of the same height. The two elongated frame members on either side of the two centrally located horizontally extending members are labeled as 27 and have a larger height than the centrally located horizontally extending members, which are labeled as 31. Thus, both horizontally extending members 31 are of the same height and both elongated frame members 27 are of the same height. Outside of the horizontally extending members are outer members which are hollow and are labeled as 33.

Above the outer tubular members 33 are hollow upper portions 34. Extending crosswise between the frame members are frame supports 28, which extend crosswise under the center of each LED module 40. Although a specific frame structure has been described, other frame structures may be substituted, One or both ends of the LED therapy bed 19 has a head or face rest 20 with inner side supports 21 which support a person that is lying on the LED therapy bed 19 on their back or on their face, in order to enable the person using the LED therapy bed 19 to receive therapeutic benefits to either front, back or sides of the user. Sides of the user are treated by a user laying on one side and then, if needed, on their other side. A plurality of removable and replaceable LED modules 40 are placed in the frame of the LED therapy bed 19.

The transparent acrylic cover 49 provides a slight spacing between the user and the LEDs. The transparent acrylic cover 49 distributes the weight of the user on the frame structure of the plurality of removable and replaceable LED modules 40 The transparent acrylic cover 49 is preferably made from a clear material, such as acrylic or polycarbonate, but other materials may be used that provide equivalent or superior transparency or structural strength.

As can be additionally seen, in FIG. 2, elongated side members 24 and 26 are above legs 23. Between the elongated side members 24 and 26, elongated frame members 27 and 31 support the LED modules 40 in a curved configuration that centers the user in the center of the LED therapy bed 19. The head rest or face rest 20 supports the rear of the head of a user and can support the face of a user and provides clearance for the user to breathe through their nose or mouth. A support 29 connects an end of the LED therapy bed 19 and the head rest or face rest 20. Although one head rest or face rest 20 has been shown, the head rest or face rest 20 can be located on either end of the therapy bed. In one exemplary embodiment, the LED therapy bed 19 has thirty LED modules 40 configured in five columns and six rows, but LED therapy beds with more or less modules and a different number of columns and rows of modules may be provided. Each LED module 40 is essentially the same, but may be of different shape or size, and each LED module 40 can be removed, replaced or swapped. Each LED module 40 is self-contained and can operate independently or together with any or all other LED modules 40. The LED modules 40 are shown and described in more detail in other figures herein.

Figure 3:
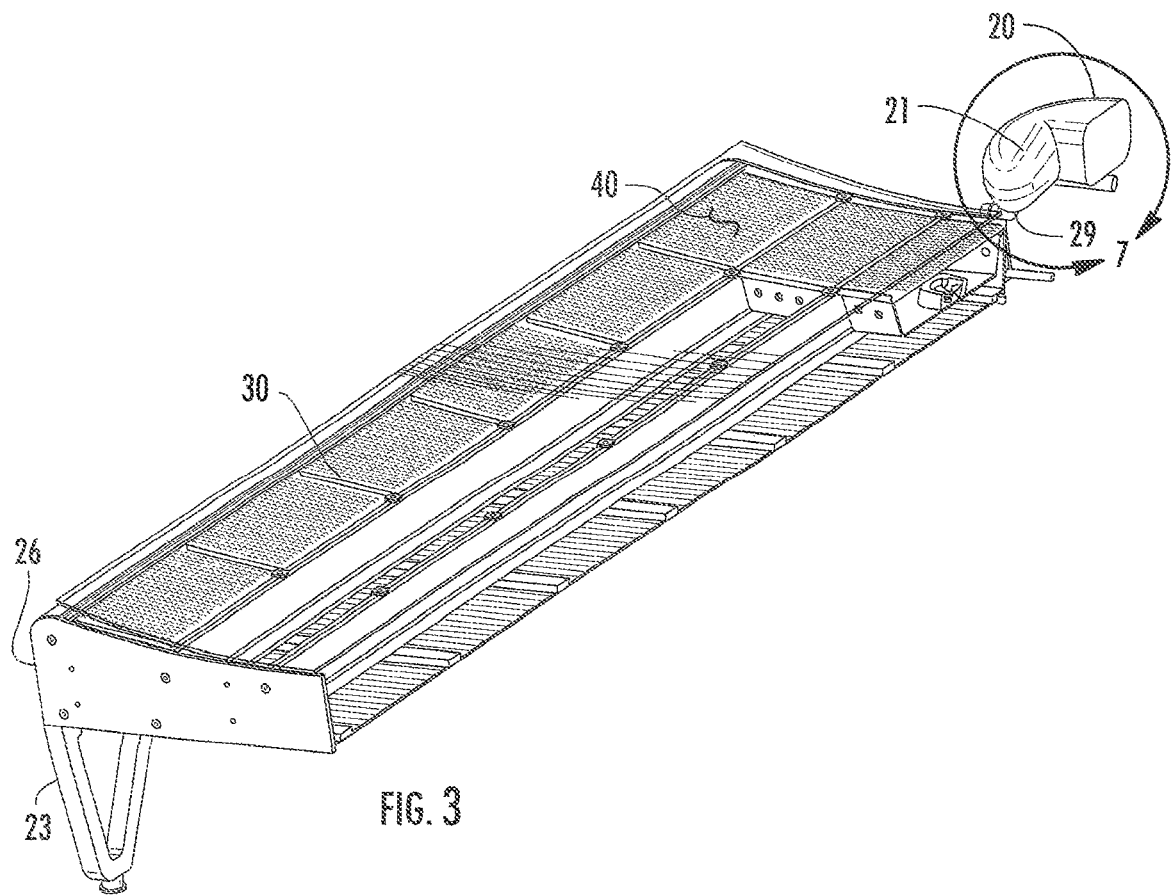
FIG. 3 illustrates a perspective cross-sectional view of the LED therapy bed, taken along lines 3-3 of FIG. 1.

Turning next to FIG. 3, this figure is a perspective view of FIG. 1, taken along line 3-3. As shown in FIG. 3, a rectangular connector 30 is provided. This connector 30 fits in the cutaway portions 45 (see FIG. 4) at the corners of each LED module 40. The corners of four modules form a rectangle which receives rectangular connector 30 to hold the LED modules 40 in place. The top of the connector 30 is below the top of the LEDs, in an exemplary embodiment.

Figure 4:
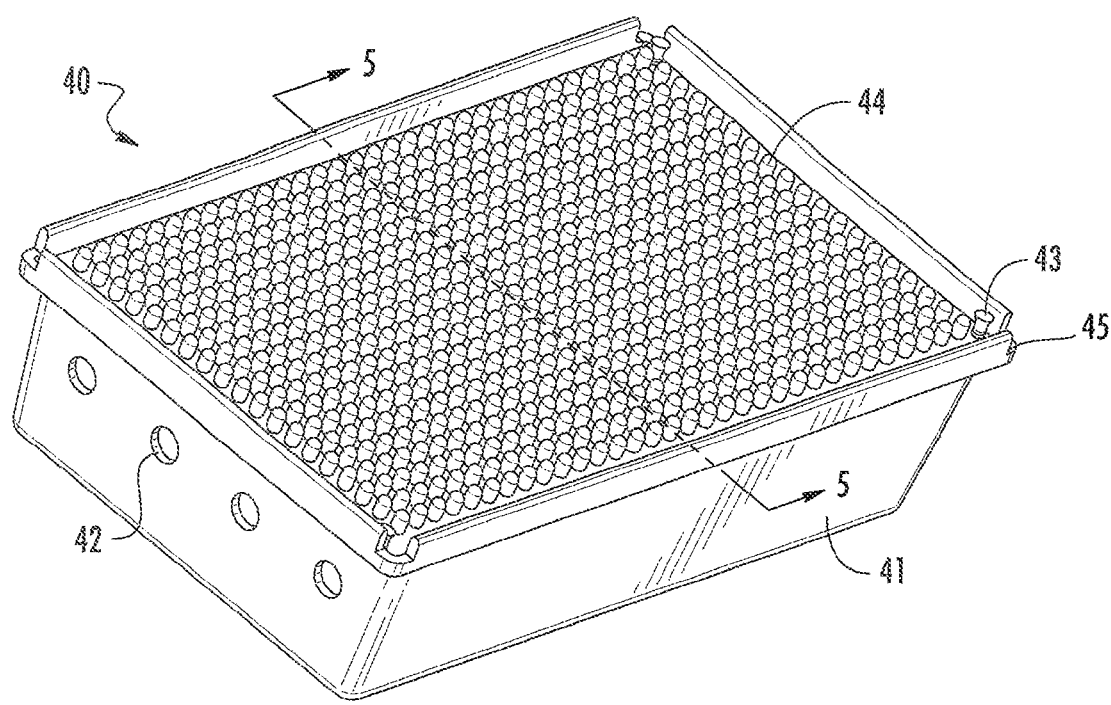
FIG. 4 illustrates a perspective view of a single LED module.

FIG. 4 illustrates a perspective view of a single LED module 40. In one exemplary embodiment, each LED module 40 has a matrix of LEDs configured in 19 by 32 columns for a total of 608 LEDs, but other embodiments of rows and columns of LEDs may be provided, instead of the particular configuration shown. The LEDs provide non-coherent light generated by an array of conventional light emitting diodes (LEDs) which are confined within a bandwidth of about 415 nm to about 940 nm. The LED array is configured in a matrix to direct the light onto a diffuse area of the user, through the acrylic layer, without utilizing an optical system, etc. The light is emitted at a preset angle to provide the most effective treatment of a user.

Housing 41 supports the internal electronics and a circuit board 46 (see FIG. 5) which supports the LEDs 44. Each individual LED 44 module 40 may be secured to the housing 41 with fasteners 43. In addition, in one exemplary embodiment, one or more of the separately controlled LED modules 40 may have electrical connections for between about 100 to about 1,000 LEDs 44.

Each LED module 40 is self-contained and independently regulates its temperature to maintain an optimal skin dilatation temperature. A current limiting device connects to the LEDs, In an exemplary embodiment, the current limiting resistor is selected to provide a deliberate increase in said skin tissue temperature of a user where the skin temperature is between 97-108 degrees F., when held continuously against or in very close proximity to a user's skin tissue for a twenty-minute period. Each LED module 40 has openings or holes 42 for venting air from the inside of the LED module 40. The holes 42 allow for cooling or heating air to be independently moved through each LED module 40 to independently regulate the temperature of each LED module 40. As shown in FIG. 4, the top portion of LED module 40 overhangs the housing 41 so that the air from the holes 42 is vented away from each LED module 40. In addition, each module has one or more fans 51 to move air within the module, in order to control the temperature of the air below acrylic cover 49, which results in control of the temperature of the top of the acrylic cover, which is in contact with the body of the user. Individual control of the temperature of the air above and below the acrylic cover is important because different portions of a user's body put out more heat than other portions. For example, a user's legs may put out more heat than the user's trunk; whereas the user's arms may put out more heat than the user's legs, etc. As an alternative, the LED therapy bed 19 may be formed from two modules. In addition, a second set of modules may be lowered onto or otherwise placed on the other side of the user to treat both sides of the user at the same time. Moreover, the bed or upper and lower beds may be vertically oriented or oriented at an angle to the vertical or horizontal.

Figure 5:
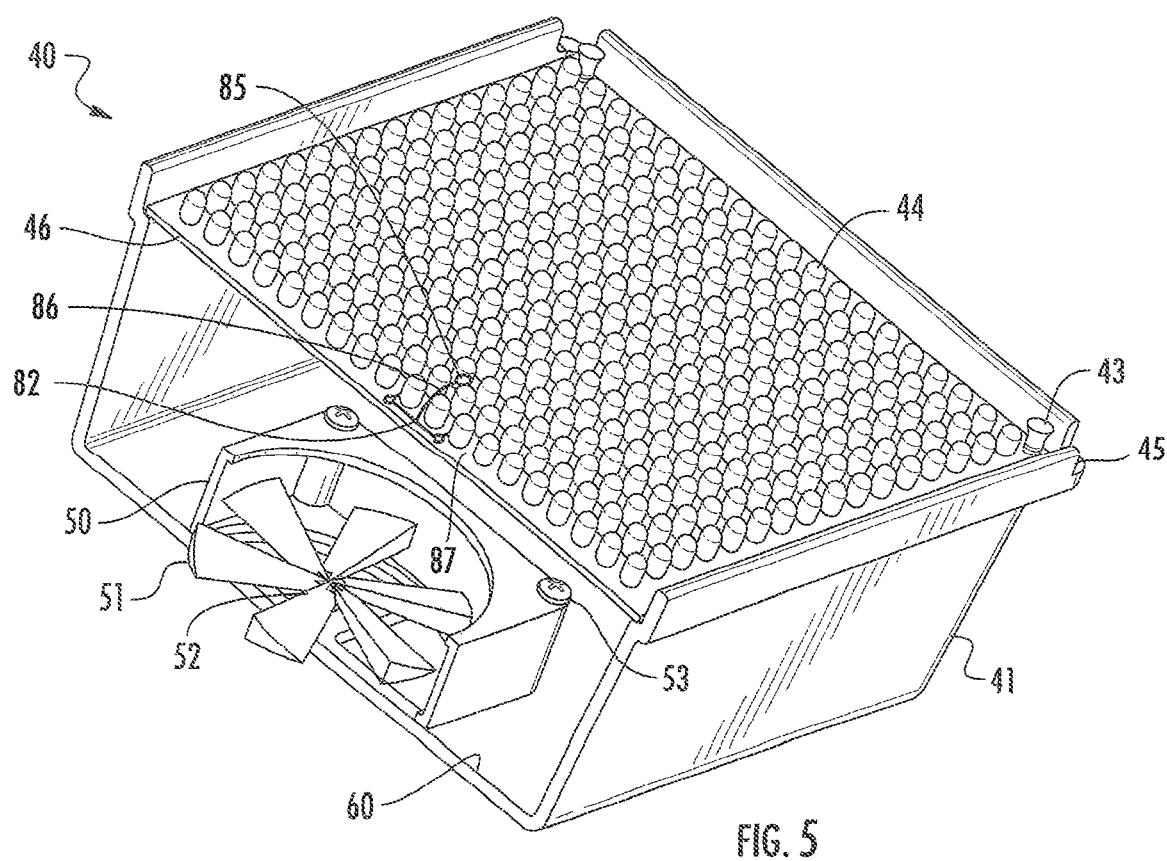
FIG. 5 illustrates a perspective sectional view of the single LED module, as taken along line 5-5 of FIG. 4.

FIG. 5 shows a perspective sectional view of the single LED module 40 from FIG. 4, taken along line 5-5 in FIG. 4. Each module 40 can have a heating element (not shown) that can pre-heat each module independently in order to reduce the time required to obtain the desired therapy temperature for a particular user. A thermistor, other heat sensor or temperature sensor 85 is located at the top of each LED module 40 to determine the temperature of each LED module 40. The thermistor, other heat sensor or temperature sensor 85 sits on a frame and is supported on legs 82. An illustration of the thermistor or other heat or temperature sensor can be found in FIGS. 9 and 10.

A controller is located either within each LED module 40 or at a separate master location. The controller measures the temperatures through sensors 85 and operates the fan 51 that is connected to a motor 52 found in compartment 50 at the bottom of the LED module 40. The fan 51 has blades and the fan speed changes to maintain the surface temperature of the LEDs 44 at the underside of acrylic cover 49. The fan compartment 50 is kept in place by screws 53 or is otherwise secured to the housing 41 of LED module 40. The regulation of the fan speed and cooling is required because the LEDs 44 are overdriven to create heat that is conducted to the skin of the user to provide heat in addition to the light therapy.

In some exemplary embodiments, the power applied to the bank of LEDs is through an LED driver. The LED driver can be in a variety of forms, from a simple resistor to a transistor, SCR, current driver, Diac, Triac or other solid-state device. The power to a module of LEDs or to each LED 44 is supplied at a desired power or current, as controlled by the controller. The current regulating or limiting device is used to consistently limit the current to the LEDs and provide both even illumination and the specific temperatures needed. Because the LEDs are often driven beyond their normal level of illumination, the LEDs produce excessive heat, Excessive heat is exhausted from each LED module 40 through holes 42, as a result of the air flow created by fan 51.

Different wavelengths of light and combinations of wavelengths of light have been shown to provide various treatments including, but not limited to:

1. Treatment of wrinkles/anti-aging, and to reduce pore size: about 605 nm, about 630 nm, about 660 nm and about 850-855 nm.
2. Pain relief including carpal-tunnel and arthritic pain: about 630 nm, about 660 nm, about 850-855 nm and about 940 nm.
3. Treat acne and heal burn victims: about 415 nm or about 460-about 465 nm, about 630 or 660 nm and about 850-about 855 nm.
4. Rosacea: about 415 nm or about 460-465 nm, about 630 nm, about 660 nm and about 850-855 nm.
5. MRSA: about 415 nm or about 460-465 nm and about 850-855 nm.
6. Treat swelling and inflammation of the brain caused by severe head trauma: about 850-about 855 nm.
7. Psoriasis+Eczema (used w/serum): about 630 nm, about 660 nm, about 850-855 nm and about 940 nm.
8. Post-op to reduce scarring, bruising, healing time, pain, inflammation and redness: about 630 nm, about 660 nm, about 850-855 nm, and about 940 nm.
9. Reverse blindness caused by diabetes: about 630 nm, about 660 nm, about 850-855 nm, and about 940 nm.
10. Reverse macular degeneration: about 630 nm, about 660 nm, about 850-855 nm, and about 940 nm.
11. Heal sores in the mouth caused by chemo-therapy: about 630 nm, about 660 nm, about 850-855 nm, and about 940 nm.
12. Skin cancer: about 630 nm, about 660 nm, about 850-855 nm, and about 940 nm,
13. Bruising: about 630 nm, about 660 nm, about 850-855 nm, and about 940 nm.
14. Sinuses: about 630 nm, about 660 nm, about 850-855 nm, and about 940 nm.
15. Bell's Palsy: about 630 nm, about 660 nm, about 850-855 nm, about 940 nm, about 605 about 630 nm, about 660 nm, and about 850-855 nm.
16. Heal the chest after open-heart surgery: about 850-855 nm.
17. Help to re-grow hair: about 630 nm, about 660 nm, about 850-855 nm, and about 940 nm,
18. Fibromyalgia: about 630 nm, about 660 nm, about 850-855 nm, about 940 nm and about 605 nm, about 630 nm, about 660 nm, and about 850-855 nm.
19. Increase the amount of measurable Nitric Oxide: about 630 nm, about 660 nm, about 850-855 nm, and about 940 nm.
20. Increased blood circulation: about 630 nm, about 660 nm, about 850-855 nm, and about 940 nm.
21. Pigmentation and age spots: about 605 nm, about 630 nm, about 660 nm, and about 850-855 nm.
22. Highly statistically significant reduction in both systolic and diastolic blood pressure by using the wavelengths 630 nm, 660 mn, 855 nm and 940 nm, together, and at exactly the same time for the entire tune of the treatment of the patient.

The plurality of light can have a small variation between the light frequencies, such as about 625 nm, about 630 nm and about 635 nm, by using LEDs with different dispersion and intensities. These light frequencies, about 625 nm, about 630 nm and about 635 nm can be combined with a light frequency of about 415 nm that kill bacteria to provide optimal benefit.

Although specific wavelengths are described above, the wavelengths can be modified, if desired. In addition, although the term "about" is used in the specification when listing specific wavelengths, the term "about" is used because manufacturing tolerances may differ and because a very similar but not exact wavelength may work as well as the listed wavelength.

Figure 6:
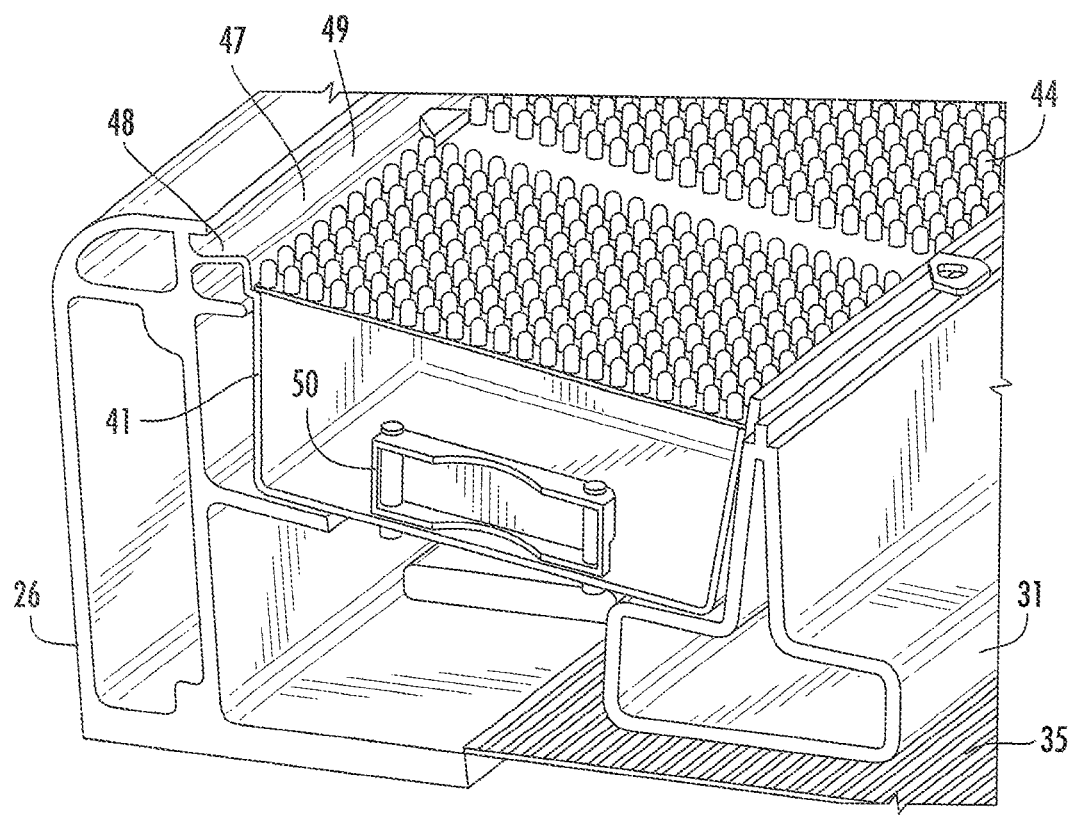
FIG. 6 illustrates a detailed view of the LED module according to detail 6, identified in FIG. 2.

FIG. 6 shows a detailed view of the LED module 40 from the detail 6 identified in FIG. 2. The LED module 40 is shown installed and retained in the top of side frame member 26. At the top of side frame member 26 is a hollow upper portion 34 (see FIG. 2). As further shown in FIG. 6, a side of the acrylic cover 49 rests on a rubber strip 47 and is kept in place from moving upwardly by overhang 48 of the hollow upper portion 34 of side frame member 26. These sections show the fan compartment 50 that provides air flow to maintain the temperature of the LED module 40, and in particular, to control the air temperature at the bottom and top of the LEDs which are beneath acrylic cover 49. Below rails 28 is a mesh fabric 35 which is made of metal or another suitable material, and which extends across most of the underside of the LED therapy bed.

Figure 7:
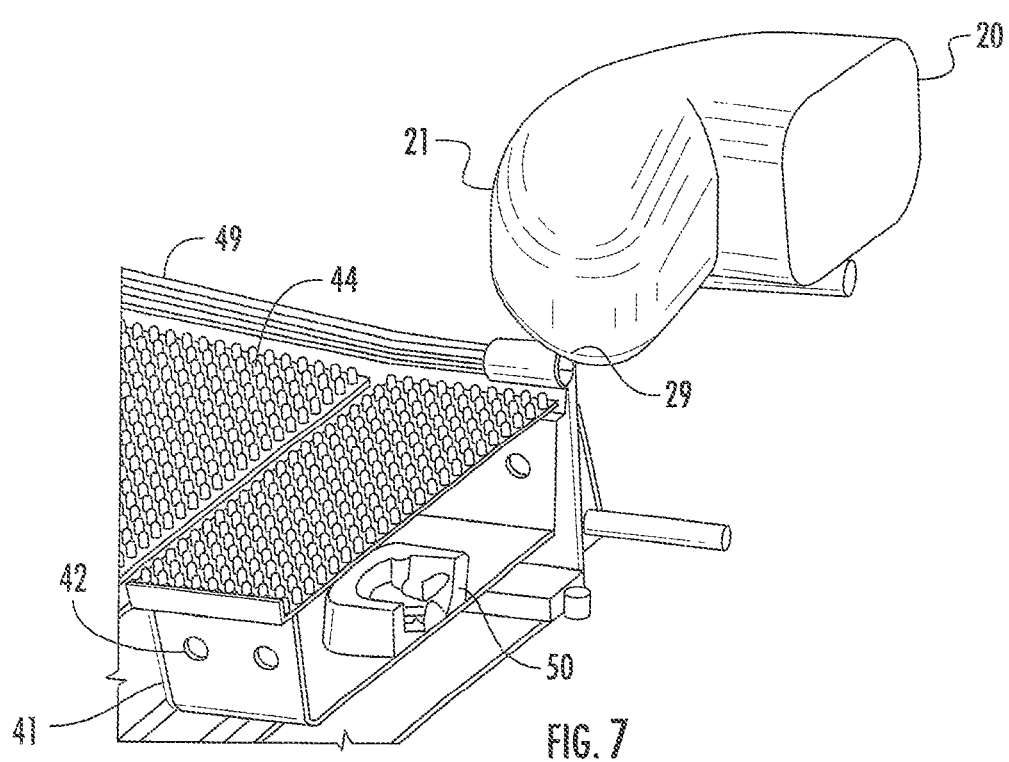
FIG. 7 illustrates a detailed view of the LED module, according to detail 7 identified in FIG. 3.

FIG. 7 shows a detailed view of the LED module 40 from the detail 7 identified in FIG. 3. The head rest or face rest 20 supports the rear of the head of a user and can support the face of a user and provides clearance for the user to breathe through their nose or mouth. A support 29 is connected between frame member 26 of the LED therapy bed 19 and the head rest or face rest 20. Although a frame is shown supporting the modules, other different frames may be substituted. In addition, although a plurality of modules 40 are shown to be located below the user, the modules 40 can also be placed above the user. In addition, sets of modules 40 can be place both above and below the user, as well as to cover the sides of the user. Moreover, although the modules 40 are described as being, essential horizontal, they can alternatively he placed in a vertical orientation or at an angle from the vertical or horizontal axes.

Figure 8:
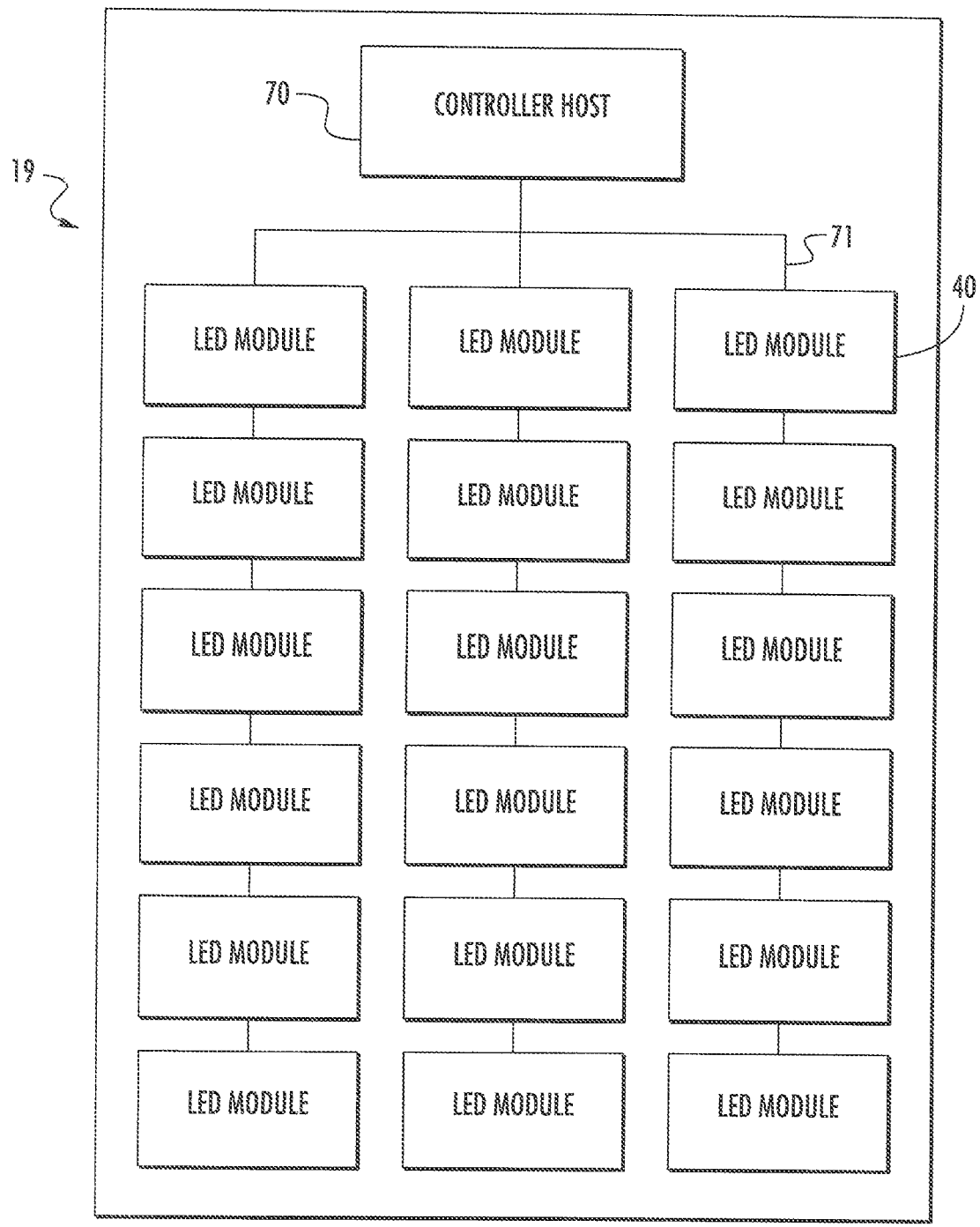
FIG. 8 illustrates a block diagram of the LED therapy bed according to an exemplary embodiment.

FIG. 8 shows a block diagram of the LED therapy bed 19. A controller 70 is wired at 71 to each of the LED modules 40. The connection from the controller 70 to the LED modules 40 can be a direct connection to each LED module 40 or can be connected in a serial or daisy chain method. The controller 70 is the master controller and each LED module 40 is a slave unit to controller 70. The host operates the display and a keyboard or knobs that accept user input, and operates the display, indicators, sound making devices etc., and the slave unit(s). Each slave LED module 40 has their own controller that controls the LEDs, fan, and monitors the temperature sensors.

Figure 9:
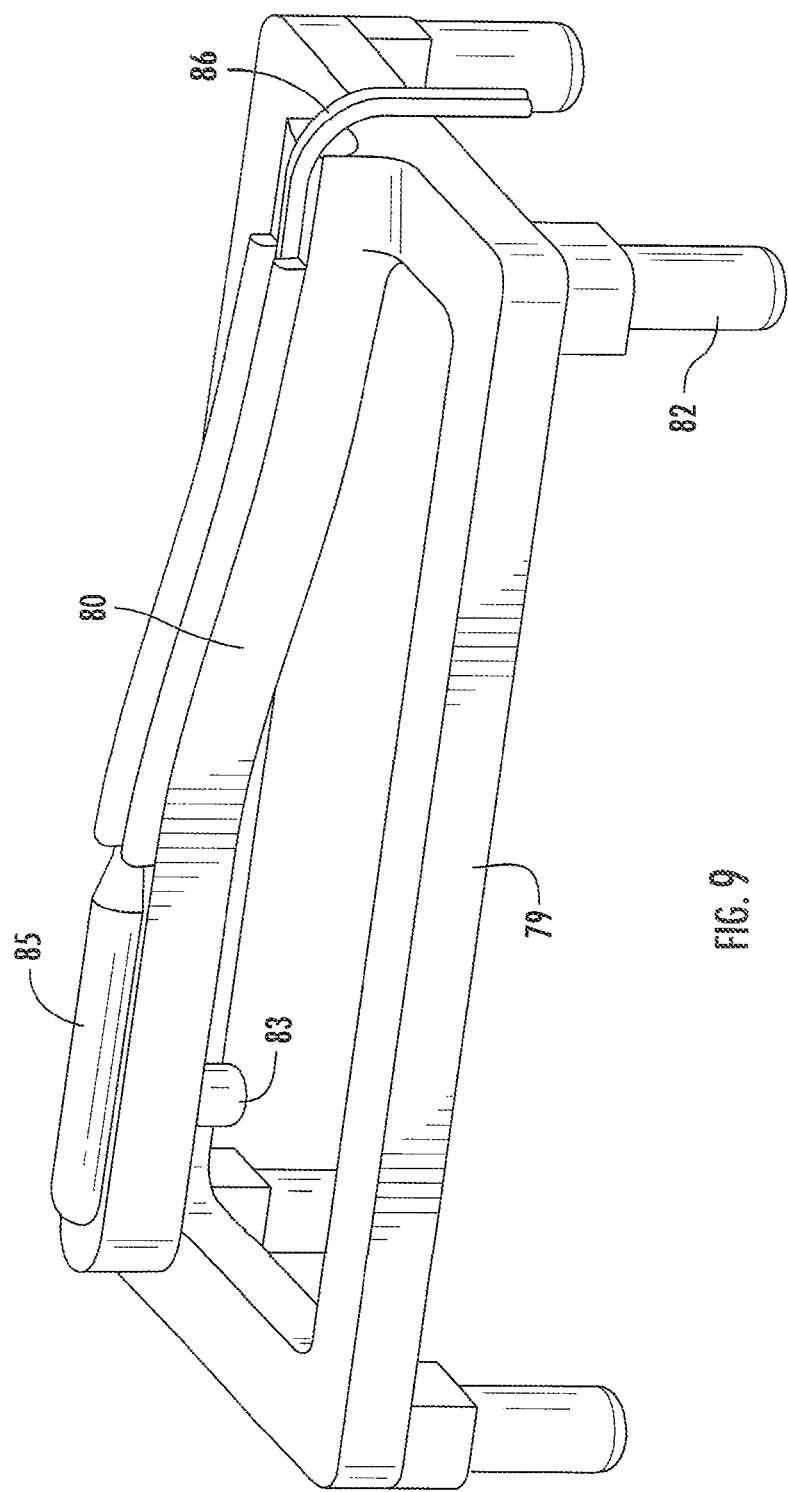
FIG. 9 illustrates the thermistor temperature sensor of FIG. 5, in greater detail.
Figure 10:
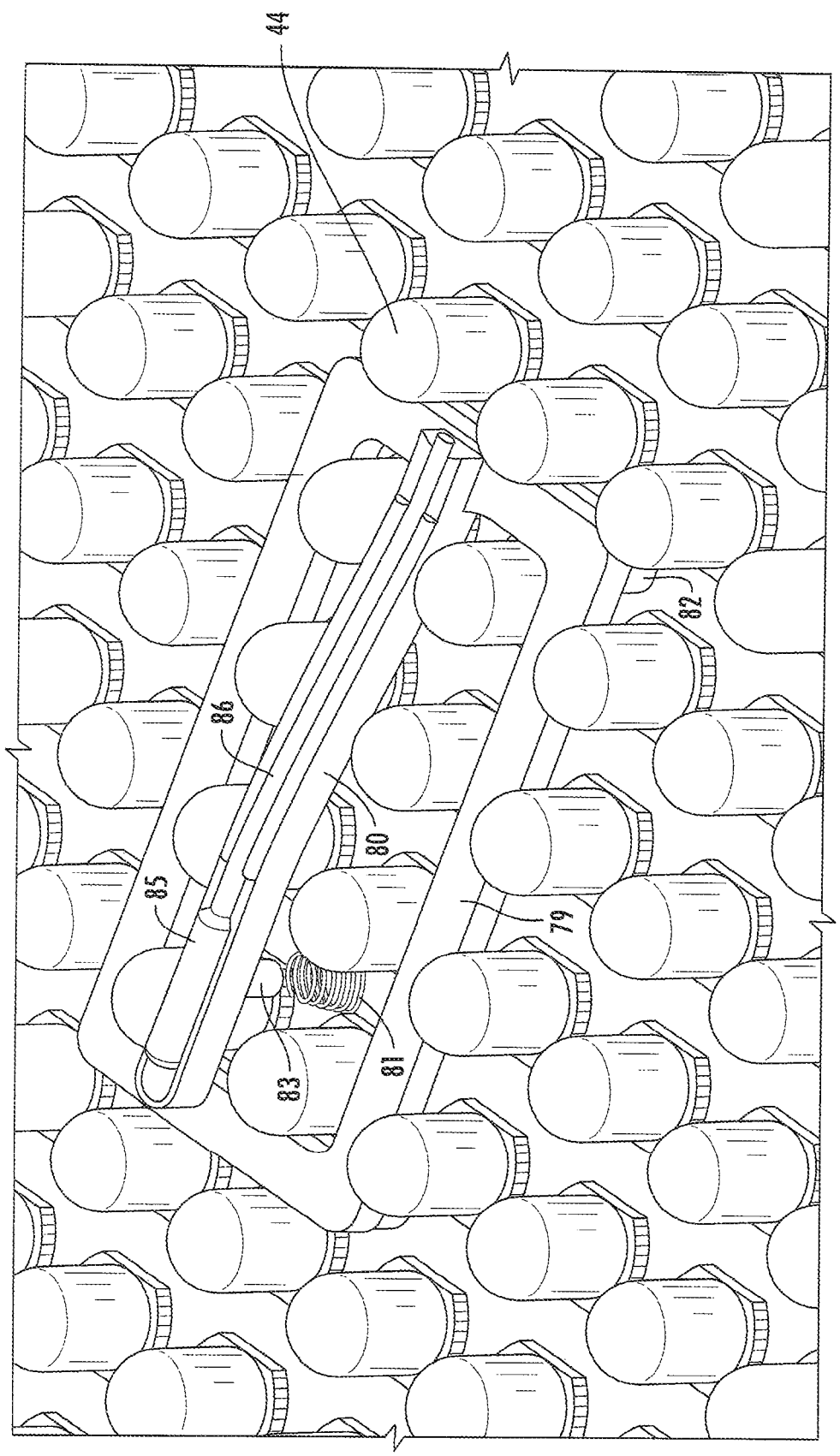
FIG. 10 illustrates the thermistor thermal sensor of FIG. 9, placed in an LED module.

Turning to FIGS. 9 and 10, the temperature sensor 85 is located at the end of a flexible arm 80 that rests on or is secured on the LED matrix circuit board via a support structure. The flexible arm 80 retains the temperature sensor 85, which may be a thermistor, in conductive contact or nearly conductive contact with the underside of the transparent acrylic cover 49 and accommodates some flexing of the transparent acrylic cover 49 that is supported, on the frame containing the LEDs 44. It is also contemplated that a thermal image temperature sensor can be used that does not rely upon conductive contact with the underside of the transparent acrylic cover 49. On the underside of the flexible arm 80 is a projection 83. This projection 83 may press downwardly onto the top of spring 81 when the arm is downwardly flexed. The thermistor 85 or equivalent rests in a groove in the top surface of the flexible arm 80. A wire or wires 86 extend from thermistor 85 across the flexible arm 80 and down to the printed circuit board (PCB) that the LEDs 44 are supported on. The flexible arm 80 is supported on a frame 79 which rests on legs 82. The frame is located between the LEDS 44 and the top of thermistor 85 is just below the top of the LEDs 44. While one temperature sensor is shown in this exemplary embodiment, multiple temperature sensors can be placed in the LED array to the underside of the transparent acrylic cover 49. Multiple temperature sensors 85 allow for reduction in the conduction of heat/cooling from a part of the user's body placed on the transparent acrylic cover 49. In addition to temperature sensors placed between the LEDs and below the transparent acrylic cover 49, additional temperature sensors can be located on the (PCB) and/or elsewhere within the LED module. The temperature sensors 85 communicate with the module where a controller 70 in each module, or a central controller, which operates one or more cooling fans 51 to maintain the temperature of the module 40.

At least one temperature sensor 85 is held in near contact with the bottom surface of the transparent acrylic cover 49 by being located just below the top of the LEDs 44. As previously described, each LED module 40 has six-hundred and eight LEDs but more or less than the six-hundred and eight LEDs may be provided. The number of wavelengths of the LEDs utilized is selected based upon the desired therapy. In addition, the LEDs can be fabricated with an internal cluster of LEDs and the transmission color of each individual LED 44 can be changed, based upon the desired therapy. In an exemplary embodiment, a plurality of different colored LEDs may be placed in a repeating pattern.

Skin and other body tissues have the ability to absorb light and use it as a source of energy to stimulate cellular regeneration. The light rays that are emitted from the device are beneficial for your skin, as they contain no UV rays. The problem with getting these same light rays from the sun is that you also get the harmful UV rays. These harmful rays can do more damage to your skin than good. With LEDs, when the correct wavelengths of light are closely and intensely flowed into the body at the proper temperatures, collagen and elastin are produced by cells called Fibroblasts. Inside these cells is a smaller cellular structure called Mitochondria.

Figure 11:
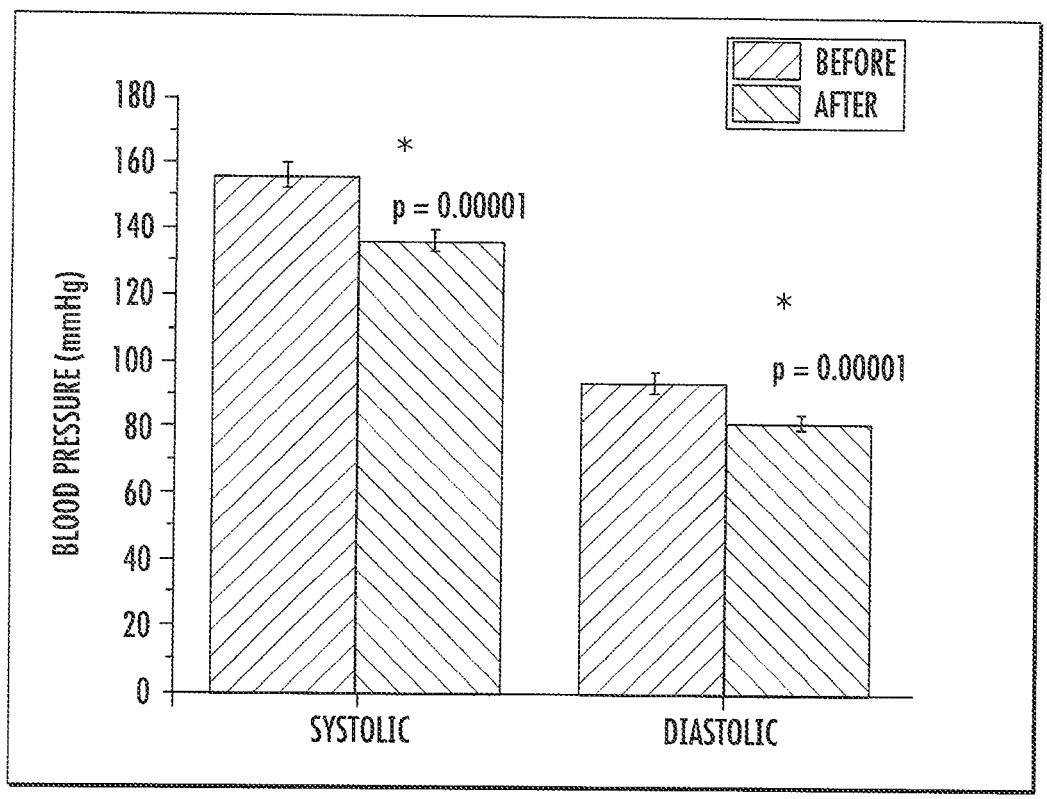
FIG. 11 illustrates a graph illustrating a baseline blood pressure prior to use of the invention. as well as the results of using the invention, which provides a highly statistically significant reduction in both

As shown in the chart illustrated in FIG. 11, the differences in systolic and diastolic blood pressure before and after 8 weeks of treatment with the LED light bed. Data are average ±SEM from 40 subjects. Baseline blood pressure prior to the first light bed session was 0±4.1 mmHg systolic and 9.1±2.7 mmHg diastolic. After 8 weeks, of 40-minute sessions three times per week, there was a highly statistically significant reduction of both systolic and diastolic blood pressure of 136.3±3 mmHg and 82±2.4 mmHg respectively. The twenty mmHg reduction in systolic blood pressure and 11 mmHg reduction in diastolic blood pressure after just 8 weeks is both impressive and clinically important. This data is illustrated in FIG. 11.

Figure 12:
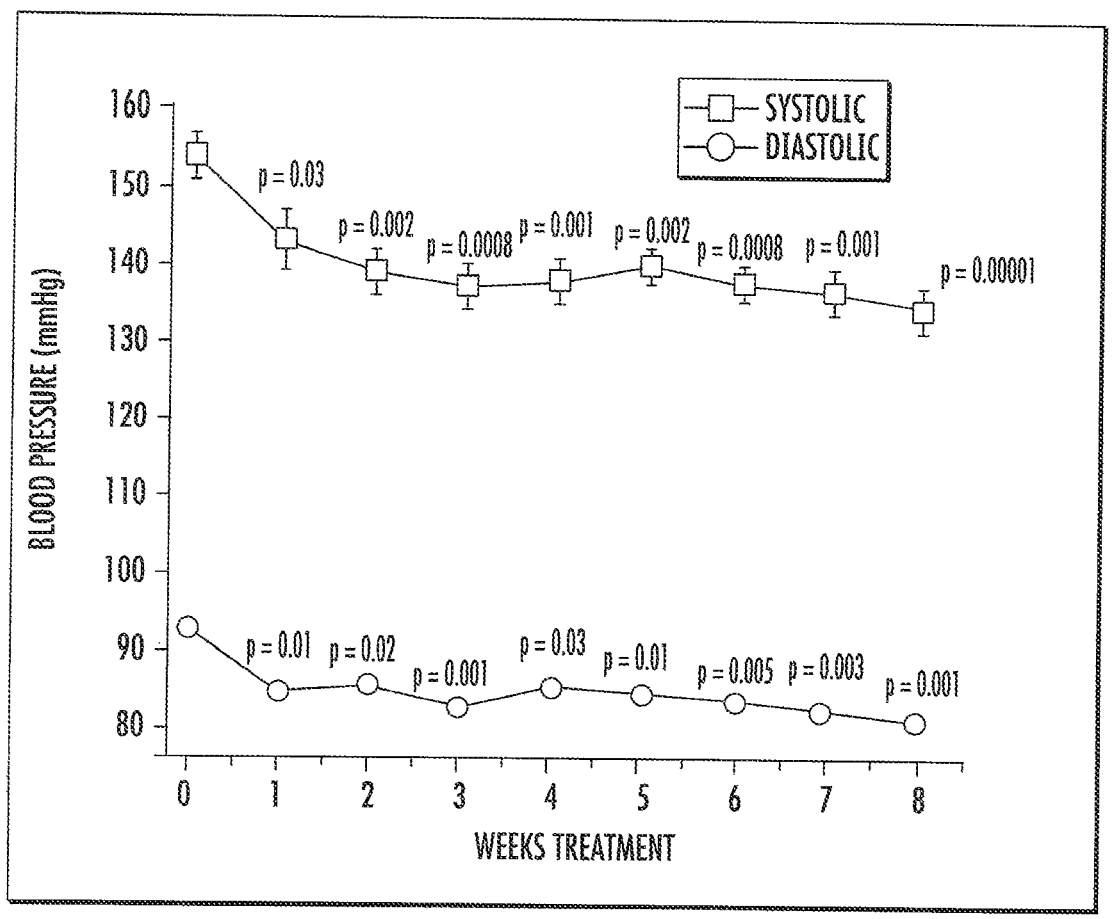
FIG. 12 illustrates a graph of the acute changes to blood pressure provided by the instant invention.

As shown in the graph illustrated in FIG. 12, the weekly changes in blood pressure from three times per week treatment with LED light bed are illustrated. Data are average ±SEM from 40 subjects. In order to investigate the acute changes in blood pressure from the LED bed, the blood pressure was recorded before and after each treatment. Subjects laid in the bed three times per week for 8 weeks. The average of systolic and diastolic blood pressure was recorded and graphed at the end of the third treatment after each week. As shown in FIG. 12 there vas a highly statistically significant reduction in both systolic and diastolic blood pressure just after 3 sessions on the LED bed. Subsequent treatments appeared to lower blood pressure even more (not statistically significant) and maintained the initial drop in blood pressure. However, after 8 weeks there was an additional 9 mmHg drop in systolic pressure and an additional 3 mmHg decrease in diastolic blood pressure from week 1 to week 8. Including and after one week treatment, there remained a significant reduction in blood pressure throughout the study. To investigate the long-term effects of the LED light bed on steady state blood pressure, forty subjects with hypertension or pre-hypertension were enrolled in an 8 week study.

Figure 13:
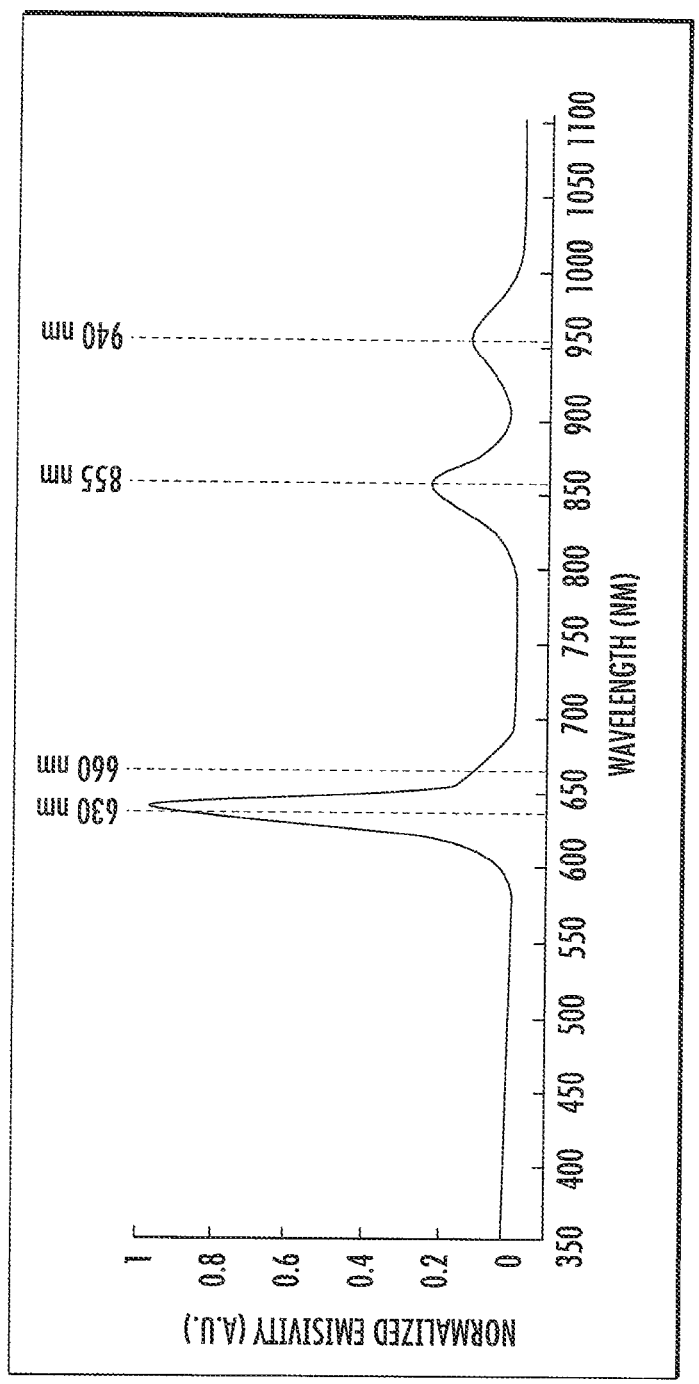
FIG. 13 illustrates a graph of VIS-NIR emission spectrum of the LED Therapy bed.

As shown in the graph illustrated in FIG. 13, a VIS-NIR emission spectrum of the LED-bed is illustrated, related to lowering of high blood pressure. This study was approved by Salus IRB (study protocol LightStim BP). The study was registered at clinicaltrials.gov (NCT04006158). The major component of the setup was the light illuminating bed (LightStim Professional LED Bed; of LED Intellectual Properties LLC), which is an FDA-approved over-the-counter device that emits energy in the visible and IR spectrum. LightStim bed is intended to provide topical light therapy for the purpose of temporary relief of minor muscle and joint pain and stiffness, minor arthritis pain or muscle spasm, the temporary increase in local blood circulation, and the temporary relaxation of muscles. The recommended subject exposure time (session time) is 20 minutes on each side of the body. The illuminator surface comprised 30 independent illuminator panels emitting at four wavelength bands peaked at 630 nm, 660 nm, 855 nm, and 940 nm. The integral emission spectrum of the illuminator panel was measured by a fiber optic spectrometer (Avaspec-2048, Avantes) and is presented in FIG. 13.

Thus, specific exemplary embodiments of a LED therapy bed 19 have been disclosed. It should be apparent, however, to those skilled in the art that many more modifications besides those described herein are possible without departing from the inventive concepts contained herein. The inventive subject matter, therefore, is not to be restricted except in the spirit of the appended claims.

What is claimed is:

1. A method of lowering both systolic and diastolic blood pressure as a process of using an LED therapy bed to lower blood pressure of an individual; the method comprising the steps of:

providing a plurality of LED modules;

providing a frame supporting the LED therapy bed;

the step of each LED module including a plurality of different LEDs regulated by one or more current limiting circuits;

the step of the plurality of different LEDs being configured to be overdriven to increase light output beyond normal operating intensity and to further produce thermal heat from the plurality of LEDs, in order to produce a skin temperature of a user between 101 and 108 degrees Fahrenheit from direct thermal conduction;

the step of providing an acrylic cover over the LEDs in the modules;

the step of each of the LED modules further including at least one thermal sensor placed between the LEDs and it conductive contact with the acrylic cover;

the step of the thermal sensor being supported by and resting within a flexible arm that is located between the LEDs of each module;

the step of the thermal sensor locally sensing a temperature adjacent the underside of the acrylic cover which is over the LEDs within a module;

the step of each of the LED modules further including at least one fan wherein the fan speed is regulated directly or indirectly by said at least one thermal sensor;

the step of providing a master controller that controls the LEDs, wherein there is the at least one fan and the at least one thermal sensor in each said module;

the step of the temperature of each module, LED or cluster of LEDs is separately controlled while each module or LED or cluster of LEDs is providing treatment;

the step of the LEDs, thermal sensor, current limiting circuit, and fan are controlled by the master controller to raise and maintain the skin temperature of all areas of the user's body being treated by the LED therapy bed from a starting temperature to a same therapeutic temperature in the range of 101 to 108 degree Fahrenheit;

the step of the temperature of each of the areas of the user's body being treated reaches the same therapeutic temperature at the same time; and lowers the blood pressure of a patient through the use of wavelengths of 630 nm, 660 nm, 855 nm, and 940 nm together and at exactly the same time; and the method of lowering both systolic and diastolic blood pressure using the LED therapy bed lowers the systolic blood pressure of a patient by 20 mm Hg and lowers the diastolic blood pressure of the patient by 11 mm HG.

2. The method of lowering both systolic and diastolic blood pressure using an LED therapy bed of claim 1; the method further comprising the step of: the light rays emitted form the LED therapy bed contain no UV rays.

* * * * *